(12) United States Patent
Spehalski

(10) Patent No.: US 8,834,453 B2
(45) Date of Patent: Sep. 16, 2014

(54) STEERABLE WOUND DRAIN DEVICE

(71) Applicant: Allegiance Corporation, McGaw Park, IL (US)

(72) Inventor: Stephan R. Spehalski, Florida, NY (US)

(73) Assignee: Allegiance Corporation, McGaw Park, IL (US)

( * ) Notice: Subject to any disclaimer, the term of this patent is extended or adjusted under 35 U.S.C. 154(b) by 0 days.

(21) Appl. No.: 14/010,321

(22) Filed: Aug. 26, 2013

(65) Prior Publication Data

US 2013/0345680 A1    Dec. 26, 2013

Related U.S. Application Data

(60) Division of application No. 12/695,854, filed on Jan. 28, 2010, now Pat. No. 8,545,481, which is a division of application No. 10/756,022, filed on Jan. 12, 2004, now Pat. No. 7,658,735, which is a continuation-in-part of application No. 09/717,664, filed on Nov. 21, 2000, now abandoned, which is a continuation-in-part of application No. 09/274,439, filed on Mar. 22, 1999, now abandoned.

(51) Int. Cl.
*A61M 27/00* (2006.01)
*A61M 1/00* (2006.01)

(52) U.S. Cl.
CPC .............. *A61M 1/008* (2013.01); *A61M 1/0088* (2013.01); *A61M 1/0031* (2013.01)
USPC .......................................... 604/543; 604/319

(58) Field of Classification Search
CPC ............ A61M 1/008; A61M 1/00588; A61M 1/0023; A61M 1/0031; A61M 1/0058; A61M 1/0084; A61M 27/00; A61B 5/01; A61B 5/1459; A61B 5/413; A61B 17/32002; A61F 2013/00536
USPC .............. 604/8–10, 43, 93.01, 129, 264–268, 604/540–544, 508, 523–536; 600/433–435, 600/585
See application file for complete search history.

(56) References Cited

U.S. PATENT DOCUMENTS

| | | | |
|---|---|---|---|
| 1,596,754 A | 8/1926 | Moschelle |
| 1,879,249 A | 9/1932 | Honsaker |
| 2,134,152 A | 10/1938 | Schwarzmayr |
| 2,450,217 A | 9/1948 | Alcorn |
| 2,498,692 A | 2/1950 | Main |
| 3,260,258 A | 7/1966 | Berman |
| 3,528,427 A | 9/1970 | Sheridan et al. |
| 3,559,641 A | 2/1971 | Lay |
| 3,582,234 A | 6/1971 | Isreeli et al. |
| 3,623,484 A | 11/1971 | Schulte |

(Continued)

FOREIGN PATENT DOCUMENTS

| FR | 2 240 026 | 8/1973 |
|---|---|---|
| GB | 105038 | 3/1917 |

*Primary Examiner* — Philip R Wiest

(57) ABSTRACT

The invention relates to a steerable wound drainage device which permits control of the positioning within the body of the device thereby affording the practitioner the ability to re-position the wound drain within the body while avoiding unnecessary trauma to surrounding tissues and organs. In one embodiment, the wound drainage device contains at least one longitudinal duct, at least one internal lumen, and at least one lateral opening communicating therewith, and an internal steering apparatus adapted to controllably position the catheter within the body.

16 Claims, 8 Drawing Sheets

(56) References Cited

U.S. PATENT DOCUMENTS

| | | | |
|---|---|---|---|
| 3,630,206 A | 12/1971 | Gingold | |
| 3,630,207 A | 12/1971 | Kahn et al. | |
| 3,860,008 A | 1/1975 | Miner et al. | |
| 3,993,080 A | 11/1976 | Loseff | |
| 4,007,743 A | 2/1977 | Blake | |
| 4,089,506 A | 5/1978 | Blake | |
| 4,307,723 A | 12/1981 | Finney | |
| 4,341,212 A | 7/1982 | Medwid | |
| 4,398,910 A | 8/1983 | Blake | |
| 4,445,897 A | 5/1984 | Ekbladh | |
| 4,465,481 A | 8/1984 | Blake | |
| 4,573,965 A | 3/1986 | Russo | |
| D288,962 S | 3/1987 | Blake | |
| 4,650,463 A | 3/1987 | LeVeen et al. | |
| 4,676,530 A | 6/1987 | Nordgren | |
| 4,692,153 A | 9/1987 | Berlin | |
| 4,717,379 A | 1/1988 | Ekholmer | |
| 4,740,195 A | 4/1988 | Lanciano | |
| 4,753,640 A | 6/1988 | Nichols et al. | |
| 4,790,810 A | 12/1988 | Pugh, Jr. | |
| 4,867,173 A | 9/1989 | Leoni | |
| 4,887,996 A | 12/1989 | Bengmark | |
| 4,913,683 A | 4/1990 | Gregory | |
| 4,976,684 A | 12/1990 | Broadnax | |
| 4,995,863 A | 2/1991 | Nichols et al. | |
| 5,021,044 A | 6/1991 | Sharkawy | |
| 5,035,764 A | 7/1991 | Blake | |
| 5,069,217 A | 12/1991 | Fleischhacker, Jr. | |
| 5,116,310 A | 5/1992 | Seder et al. | |
| 5,141,503 A | 8/1992 | Sewell, Jr. | |
| 5,160,325 A | 11/1992 | Nichols et al. | |
| 5,242,720 A | 9/1993 | Blake | |
| 5,419,761 A | 5/1995 | Narayanan et al. | |
| 5,489,269 A | 2/1996 | Aldrich et al. | |
| 5,511,965 A | 4/1996 | Batdorf et al. | |
| 5,512,045 A | 4/1996 | Gurchumelidze | |
| 5,527,279 A | 6/1996 | Imran | |
| 5,549,579 A | 8/1996 | Batdorf et al. | |
| 5,571,085 A | 11/1996 | Accisano | |
| 5,578,031 A | 11/1996 | Wilk et al. | |
| 5,607,405 A | 3/1997 | Decker et al. | |
| 5,697,911 A | 12/1997 | Yarger | |
| 5,713,849 A | 2/1998 | Bosma et al. | |
| 5,879,279 A | 3/1999 | Berger | |
| 5,944,690 A | 8/1999 | Falwell et al. | |
| 5,957,903 A | 9/1999 | Mirzaee et al. | |
| 6,099,513 A | 8/2000 | Spehalski | |
| 6,348,041 B1 | 2/2002 | Klint | |
| 6,866,657 B2 | 3/2005 | Shchervinsky | |
| 7,658,735 B2 * | 2/2010 | Spehalski | 604/543 |
| 8,545,481 B2 * | 10/2013 | Spehalski | 604/543 |

* cited by examiner

STEERABLE WOUND DRAIN DEVICE

CROSS-REFERENCED TO RELATED APPLICATION

This application is a Divisional of U.S. patent application Ser. No. 12/695,854, filed Jan. 28, 2010; which is a Divisional of U.S. patent application Ser. No. 10/756,022, filed Jan. 12, 2004, now U.S. Pat. No. 7,658,735; which is a Continuation-in-Part of U.S. patent application Ser. No. 09/717,664, filed Nov. 21, 2000, now abandoned; which is a Continuation-in-Part of U.S. patent application Ser. No. 09/274,439, filed Mar. 22, 1999, now abandoned. The disclosures of the prior applications are hereby incorporated in their entirety by reference.

FIELD OF THE INVENTION

The invention relates to the field of surgical devices. In particular, the invention relates to wound drainage catheters and systems for removal of fluids from wound sites.

BACKGROUND OF THE INVENTION

Wounds resulting from surgical procedures often produce fluid, called exudate, which needs to be drained from the wound site in order for proper healing and recovery to occur. At the conclusion of surgery, wounds are closed thereby creating the need for drainage devices which are compatible with closed surgical sites. To address this need, a variety of wound drainage devices have been developed in the past.

Wound drainage catheters typically contain a longitudinal flexible tube-like structure and features which facilitate the flow of body fluid away from the wound site. Various configurations and features have been developed in efforts to improve their performance.

Grooved or channeled wound drainage devices are known. For example, see Blake, U.S. Pat. Nos. 4,398,910 and D288,962, which disclose surgical drainage tubes with longitudinal ducts, and Miner et al., U.S. Pat. No. 3,860,008, which discloses a flat drain having a series of channels. Drainage catheters having lateral openings which permit ingress of body fluids are known. For example, see Sheridan et al., U.S. Pat. No. 3,528,427; Ekbladh et al., U.S. Pat. No. 4,445,897; and Loseff, U.S. Pat. No. 3,993,080, which disclose surgical drainage tubes having a plurality of lateral openings. Surgical drainage tubes which contain both longitudinal ducts and lateral openings are also known, such as that disclosed in LeVeen et al., U.S. Pat. No. 4,650,463.

The use of rigid removable guidewires to position catheters is known. For example, see Bosma et al., U.S. Pat. No. 5,713,849 and Bengmark, U.S. Pat. No. 4,887,996, which disclose a preconfigured catheter which contorts upon removal of the guidewire, and Nichols et al., U.S. Pat. No. 5,160,325.

Spehalski, U.S. Pat. No. 6,099,513, discloses a wound drainage catheter containing a plurality of alternating longitudinal ducts and internal lumens. This reference does not teach the use of a steerable guidewire in conjunction with a wound drainage catheter. Wound drainage catheters having longitudinal ducts, internal lumens, lateral openings and reinforcing fibers to prevent kinking are also known. See Seder et al., U.S. Pat. No. 5,116,310.

Various mechanisms to control catheter configuration within the body have been proposed. Leoni, U.S. Pat. No. 4,867,173, discloses a guide catheter having a steerable guidewire useful for cardiac procedures. Aldrich et al., U.S. Pat. No. 5,489,269, and Lanciano, U.S. Pat. No. 4,740,195, disclose catheters having a tension member positioned exterior to the distal portion of the catheter which "loops" the catheter upon applied tension. Falwell et al., U.S. Pat. No. 5,944,690, discloses a steerable catheter control mechanism comprising selectively tensioned control wires. Fleischhacker, Jr., U.S. Pat. No. 5,069,217, discloses an steerable guidewire comprising a solid core wire and wire coil. Accisano, III, U.S. Pat. No. 5,571,085, discloses a steerable catheter containing a fluid transport tube.

There exists a need in the medical field for improved wound drainage catheters and systems which operate more effectively and reduce the trauma caused to the patient. Especially useful would be a wound drainage catheter containing the fluid flow advantages of longitudinal ducts, internal lumens and lateral openings as well as the advantages of a steerable and controllable internal guidewire to aid in accurate positioning and re-positioning as well as reduce or eliminate undesirable trauma to tissues and organs surrounding the wound site.

SUMMARY OF THE INVENTION

The invention provided for herein pertains to a steerable wound drainage device which facilitates fluid flow away from the wound site and permits precise and controlled positioning of the wound drain within the body thereby affording the practitioner the ability to precisely position and re-position the wound drain within the body while avoiding undesirable trauma to surrounding tissues and organs. The device is particularly useful in draining fluids from wound sites which can benefit from precise or accurate positioning of a wound drainage catheter in a controllable manner.

Accordingly, the invention provides for a wound drainage device comprising a flexible catheter having at least one longitudinal duct and having at least one internal lumen, at least one lateral opening in communication with said internal lumen, and an internal steering apparatus structured to controllably position said catheter when placed within the body by permitting deviation of said catheter portion into a plurality of configurations and directions relative to a longitudinal axis while continually residing within said catheter. In a preferred embodiment, the wound drainage device comprises a plurality of longitudinal ducts, internal lumens, and lateral openings. In another preferred embodiment, the internal steering structured to controllably position the catheter within the body comprises a control element which is externally and manually operable by the practitioner. The invention also includes a kit comprising the wound drainage device of the invention.

In another embodiment, the invention includes a wound drainage device comprising a flexible catheter having at least one longitudinal duct and an internal steering means adapted to controllably position said catheter within the body by permitting deviation of said catheter portion into a plurality of configurations and directions relative to a longitudinal axis while said internal steering apparatus performs said controllable positioning while continually residing within said catheter.

In yet another embodiment, the invention includes a wound drainage device comprising a flexible catheter having at least one internal lumen; at least one lateral opening in communication with said internal lumen; and an internal steering apparatus structured to controllably position said catheter within the body by permitting deviation of said catheter portion into a plurality of configurations and directions relative to a longitudinal axis while continually residing within said catheter.

The invention also provides for a method of placing a wound drainage device within a body comprising inserting a wound drainage device into a site within the body, said device having a flexible catheter having at least one longitudinal duct and having at least one internal lumen; at least one lateral opening in communication with said internal lumen; and an internal steering apparatus structured to controllably position said catheter within the body by permitting deviation of said catheter portion into a plurality of configurations and directions relative to a longitudinal axis while continually residing within said catheter; and positioning the wound drainage device within the body by actuating said internal steering apparatus.

The invention provides for a method of draining a wound site in a body in need of fluid removal therefrom comprising inserting a wound drainage device into a wound site within the body, said device having a flexible catheter having at least one longitudinal duct and having at least one internal lumen; at least one lateral opening in communication with said internal lumen; and an internal steering apparatus structured to controllably position said catheter within the body by permitting deviation of said catheter portion into a plurality of configurations and, directions relative to a longitudinal axis while continually residing within said catheter; positioning the wound drainage device into position; and draining fluid from the wound site. In a further embodiment, the device can be subsequently repositioned within the body.

DETAILED DESCRIPTION OF THE INVENTION

The term "fluid" when used in the context of body fluid is meant to include any bodily fluid suitable for removal using a wound drainage device, e.g., exudate produced at a wound site, liquified fat cells, blood, and the like.

The term "site" when used in the context of placement of the wound drainage device refers to the location within the body which can benefit from drainage of fluids, e.g., a wound resulting from surgery whereby removal of fluids aids in the healing of the wound.

As used herein, the phrase "controllably position" is meant to describe the capability afforded to the device of the invention by its assembled structural components that permit deviation of the catheter portion into a plurality of configurations and directions relative to a longitudinal axis.

Figure 1:
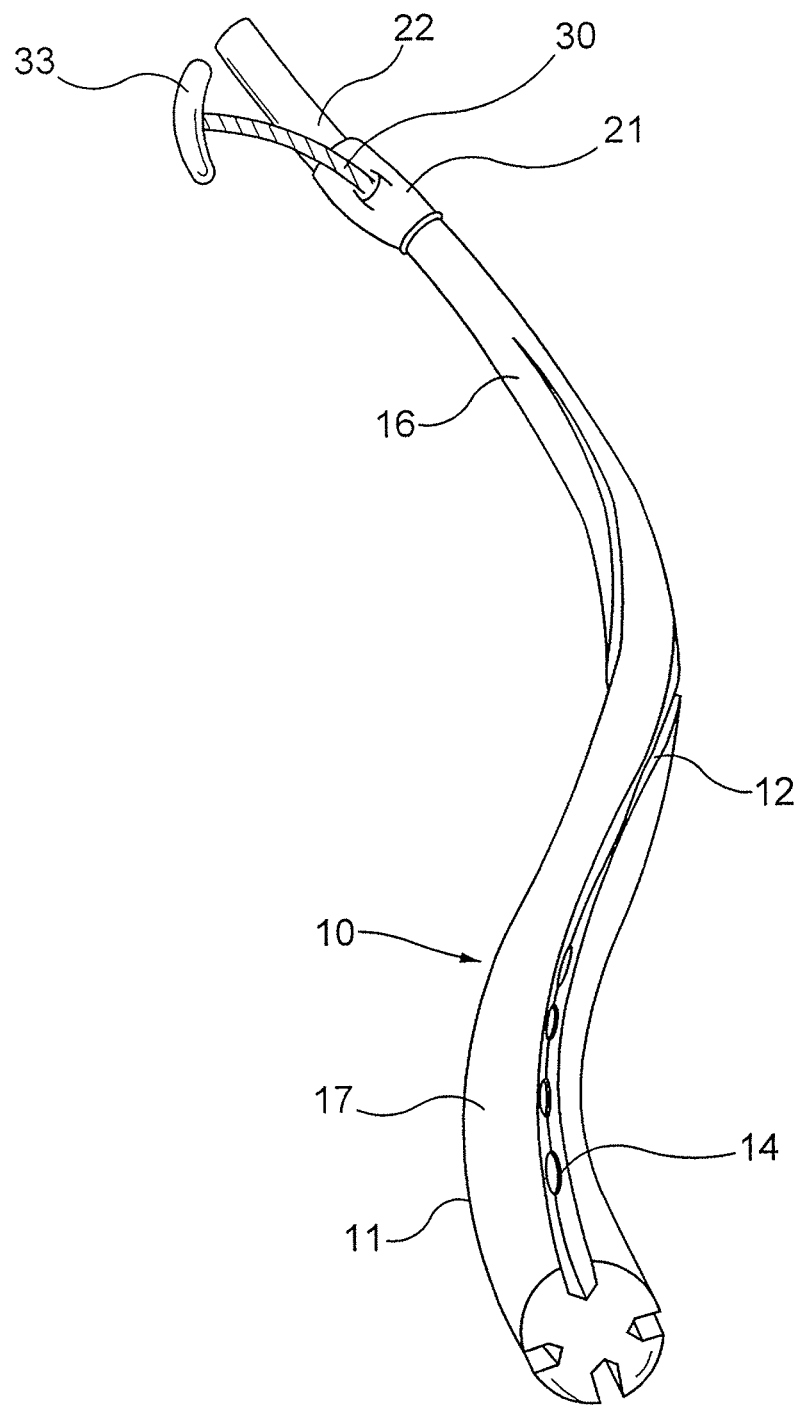
FIG. 1 is an overall view of the steerable wound drainage device according to one embodiment of the invention.
Figure 2:
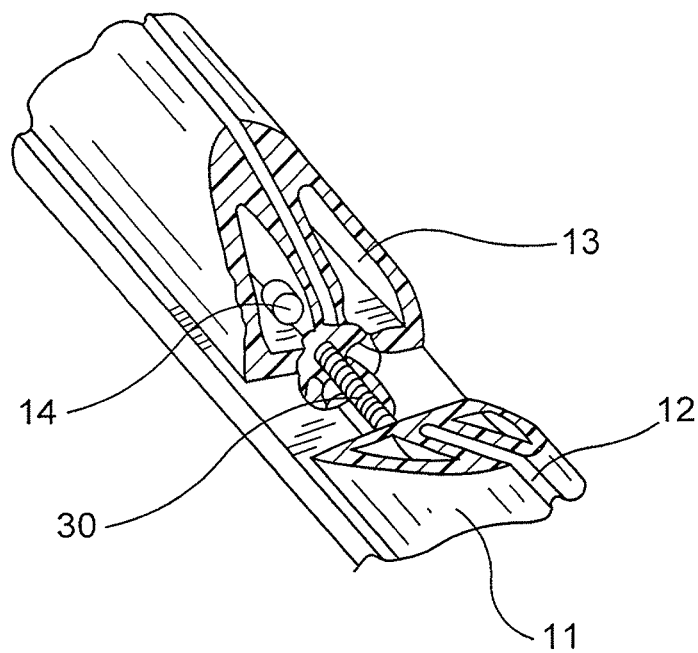
FIG. 2 is a cut-away view of a segment of the steerable wound drainage device according to one embodiment of the invention.
Figure 3:
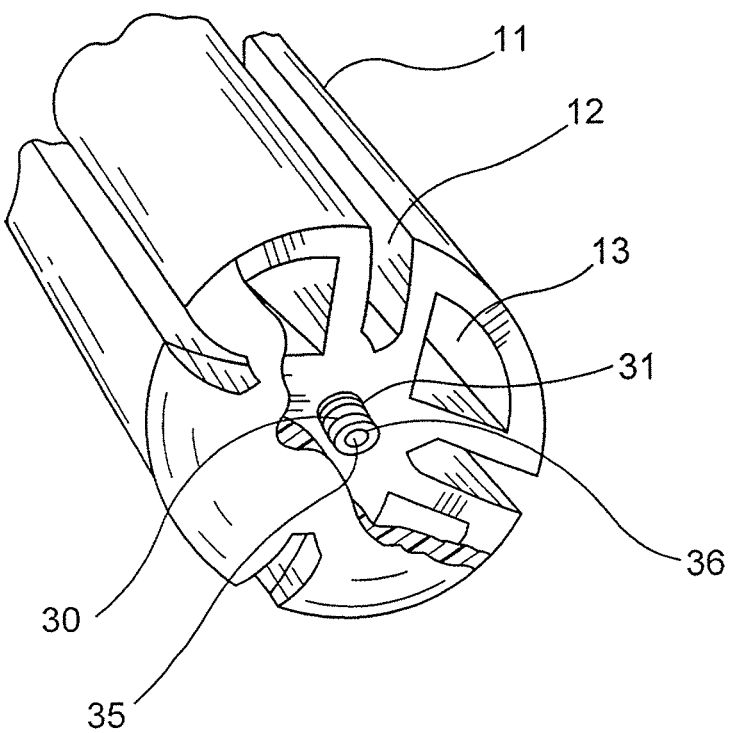
FIG. 3 is a partial cut-away view of the distal tip of a steerable wound drainage device according to one embodiment of the invention.

Referring to FIGS. 1, 2 and 3, the wound drainage device 10 of the invention generally includes a flexible catheter 11 having at least one longitudinal duct 12 and having at least one internal lumen 13 (not shown in FIG. 1), at least one lateral opening 14 in communication with said internal lumen, and an internal steering apparatus adapted to controllably position said catheter within the body. Ina preferred embodiment, the wound drainage device comprises a plurality of longitudinal ducts, internal lumens, and lateral openings. In another preferred embodiment, the internal steering apparatus adapted to controllably position the catheter within the body comprises an external control element 33 which is externally operable by the practitioner. As used herein and in the claims, the term "internal steering apparatus" includes the portion of the apparatus that is inside the catheter and the portion external to the catheter.

An important feature of the invention is the ability to controllably position the device. In other words, the assembled structural components of the device permit deviation of the catheter portion into a plurality of configurations and directions relative to a longitudinal axis. Unlike a conventional rigid stylet or guidewire placed within a catheter, the internal steering apparatus of the inventive device "guides" or "steers" the catheter portion of the device into various configurations, angles, and the like by its operation without requiring the removal of the internal steering apparatus from the catheter portion.

Figure 10:
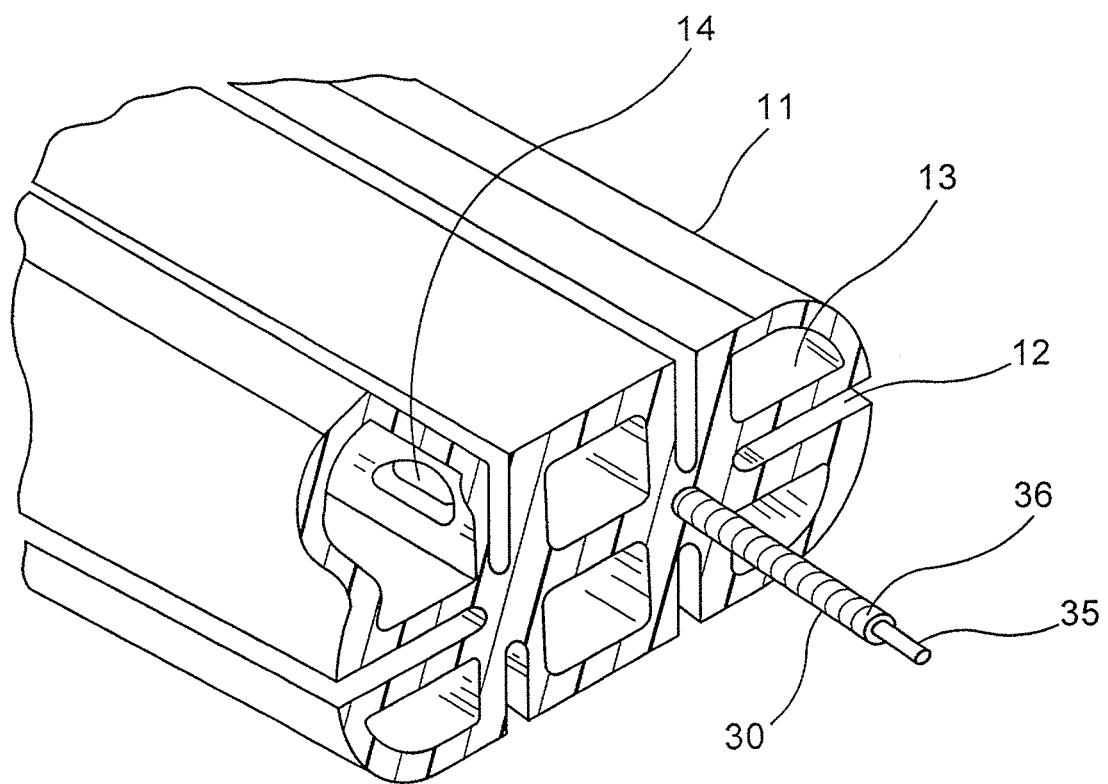
FIG. 10 is an angled perspective cross-sectional side view and partial cut-away of a portion of the device having multiple ducts and lumens; and internal steering apparatus; and catheter portion having an ovoid configuration in accordance with one embodiment of the invention.
Figure 11:
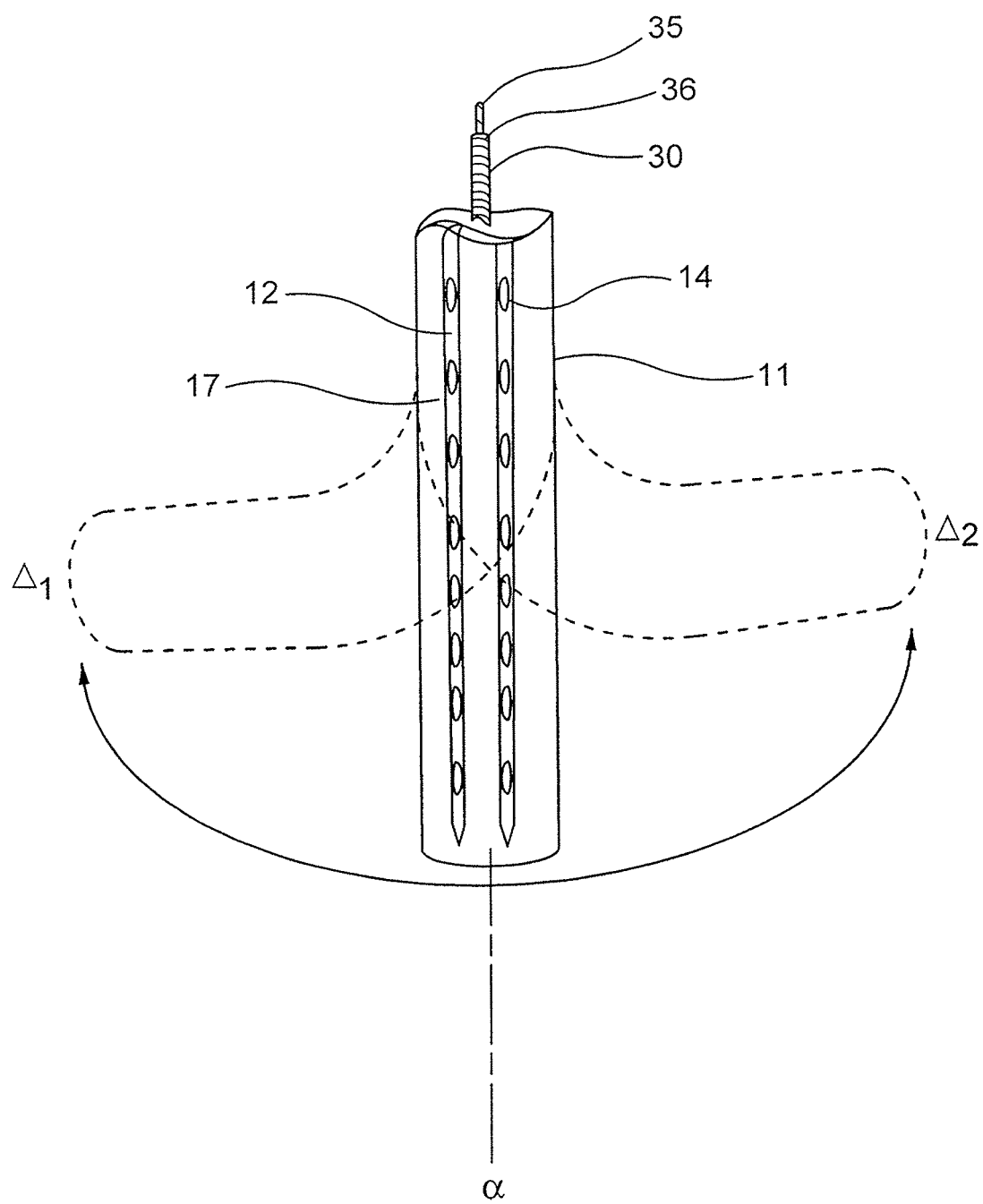
FIG. 11 is a top view of a distal portion of the catheter component of the device illustrating positional changes according to one embodiment of the invention.

Referring now to FIG. 11, there is shown an illustration of the distal portion 17 of the catheter 11, the catheter having a structure as depicted in FIG. 10. Upon actuation of the internal steering apparatus (components of which shown in FIG. 11 as numerical references 35, 36 and 30), the catheter 11 can be manipulated relative to a longitudinal axis (alpha $\alpha$). Thus, the distal portion 17 can be controllably positioned laterally between orientations delta one ($\Delta 1$) to delta two ($\Delta 2$), for example. Furthermore, the internal steering apparatus can also effect rotational configurations and various torsional configurations as well (not shown). A wide variety of positions are possible and can vary according to the design of the internal steering apparatus.

The flexible catheter component can be composed of any flexible material in accordance with the chemical and physical requirements of an internally positioned wound drainage device. Such properties include inertness and/or biocompatibility, and pliability. Examples of suitable materials which can be used include, but are not limited to, low durameter (e.g., 40-80 Shore A) plastic or silicone. The exterior surface of the catheter body can be treated with biocompatibility enhancing substances, such as heparin or polytetrafluoroethylene (PTFE or Teflon®). The catheter portion can be manufactured in accordance with any conventional technique well known in the art, such as extrusion methods.

In general, the catheter portion of the device according to the invention has a proximal 16 and distal portion 17 and contains a steering conduit 31 (see FIG. 3) adapted to accommodate the internal steering apparatus. The internal steering apparatus is contained within the catheter 11 in the distal portion 17 of the device, and the external control element 33 is located at the proximal portion 16.

The catheter portion of the device contains at least one longitudinal duct 12, at least one internal lumen 13, and at least one lateral opening 14 in communication with said internal lumen. In a preferred embodiment, the catheter portion comprises a plurality of longitudinal ducts, internal lumens and lateral openings. In an even more preferred embodiment, the catheter portion contains a plurality of alternating longitudinal ducts and internal lumens circumscribing the center of the catheter as depicted in FIGS. 1, 2 and 3, for example. One example of preferred wound drainage duct and lumen configurations is disclosed in Spehalski, U.S. Pat. No. 6,099,513, the entire text of which is incorporated herein by reference.

Longitudinal ducts 12 are formed on the catheter as externally accessible open longitudinal grooves or channels traveling along at least a portion of the length of the catheter. The size, number and shape of the longitudinal duct(s) can vary and can correspond to the longitudinal configuration of the catheter body defining the duct. The duct(s) function to prevent or inhibit obstruction of the lateral opening(s) on the catheter by surrounding tissue, thereby improving fluid movement.

Figure 4:
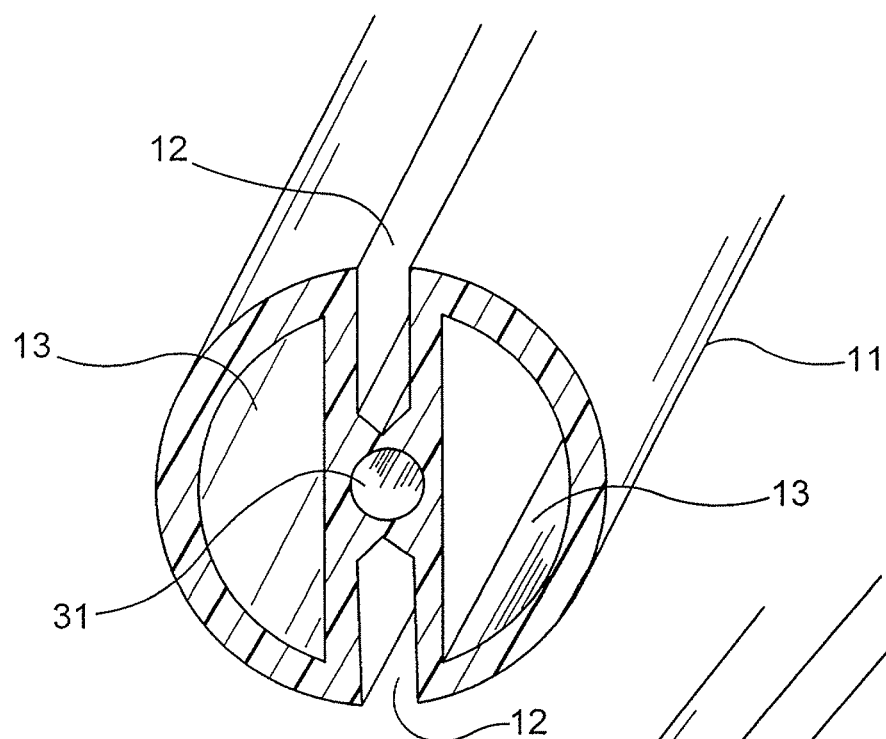
FIG. 4 is a cross-sectional view from an angled perspective of the catheter portion according to one embodiment of the invention with the internal steering apparatus removed.
Figure 5:
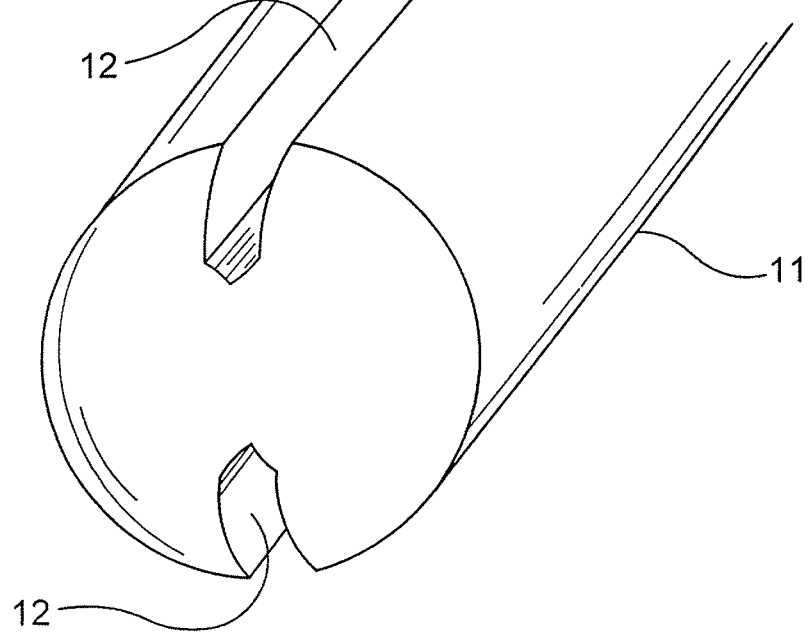
FIG. 5 is an angled perspective view of the distal end of the device according to one embodiment of the invention.

Likewise, the internal lumen(s) 13 used in the invention can vary in diameter, number and shape. Each lumen functions in communication with the lateral openings 14 which, when positioned at the wound site, permit the ingress of fluid from the surrounding area into the lumen 13. FIGS. 4 and 5 illustrate one embodiment of the invention having a catheter portion 11 with two longitudinal ducts 12 alternating with two internal lumens 13.

The number, size and location of the lateral opening(s) 14 on the catheter portion can vary and can be selected according to the desired characteristics of the wound drainage device as determined in light of the intended surgical site or nature of body fluid to be removed, or according to the patient's other particular needs.

The lateral opening(s) 14 are positioned on the surface of the catheter body. Each opening can be positioned within a longitudinal duct 12, or positioned outside the duct(s), or combinations thereof. In a preferred embodiment, the lateral opening(s) 14 communicate simultaneously with both the interior channel of the longitudinal duct(s) 12 and the lumen(s) 13.

Figure 7:
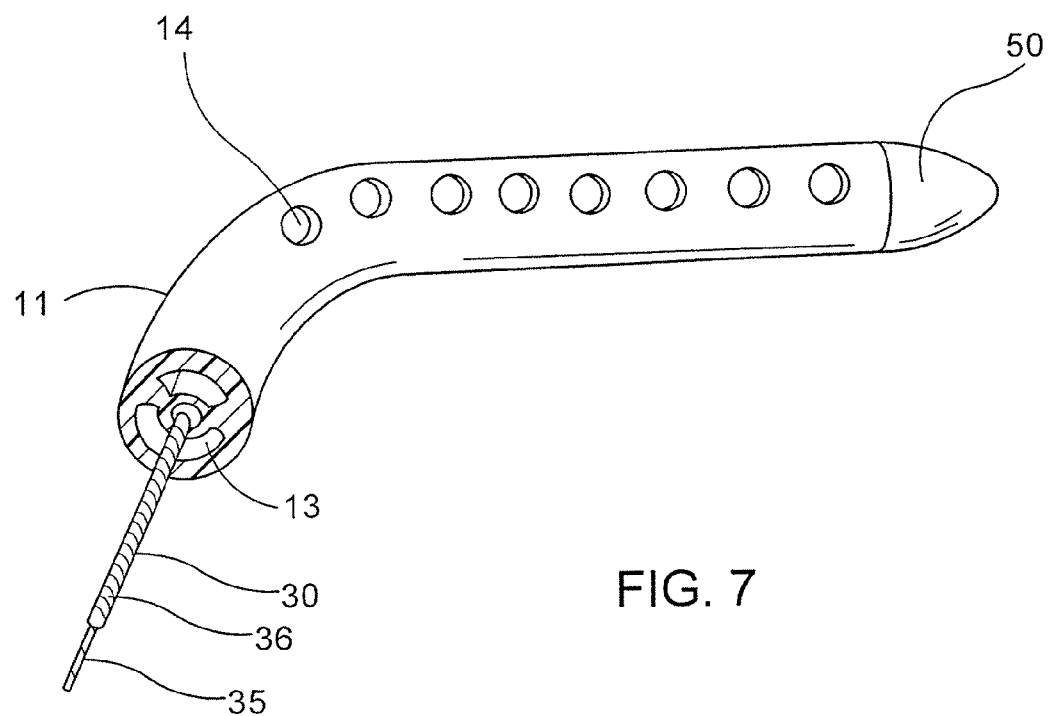
FIG. 7 is the distal portion of the device in a cross-sectional view of the interior assembly having multiple lumens and lateral openings and penetration-resistant element according to one embodiment of the invention.
Figure 8:
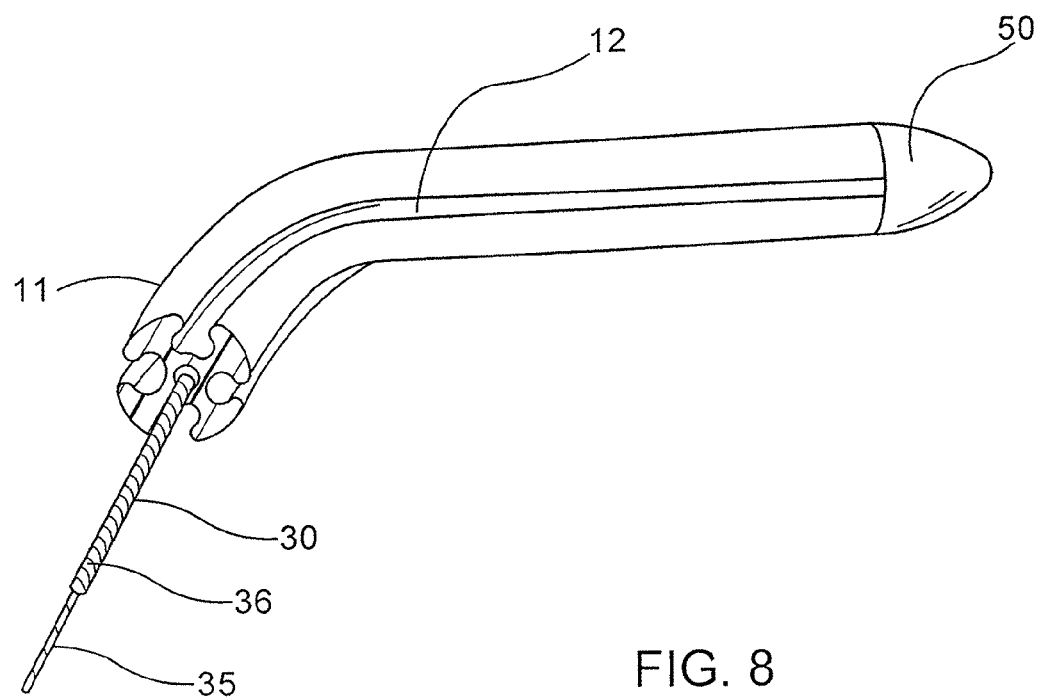
FIG. 8 is the distal portion of the device in a cross-sectional view of the interior assembly having multiple ducts and penetration-resistant element according to one embodiment of the invention.

An alternative and less preferred embodiment to the catheter portion can include catheter portions having at least one longitudinal duct without internal lumens as depicted in FIG. 8. Another alternative but less preferred embodiment includes a catheter portion having at least one internal lumen without longitudinal ducts as depicted in FIG. 7.

The proximal portion 16 of the wound drainage device 10 of the invention can contain a hub 21 which accommodates a fluid exit conduit 22, internal steering apparatus, or both. The fluid exit conduit 22 can further include one or more connectors (not shown) for attachment of additional tubing or a fluid reservoir or a suction device, for example.

The internal steering apparatus used in accordance with the invention can be any hand operated mechanism which is adapted to manipulate the configuration of a flexible catheter using components within the catheter portion. Operation of the internal steering apparatus can be performed using an external control element 33. A preferred internal steering apparatus for use with the invention is a steerable guidewire structure 30 which resides within a steering conduit 31 inside the catheter and that is coupled to an external control element 33. In FIG. 1, the external control element 33 is depicted in the form of a handle. The steerable guidewire structure 30 can include a central tension member 35 which extends the entire length of the guidewire structure and which is surrounded by a flexible coil 36. The coil 36 is reversibly flexible which, when unactuated, returns the guidewire structure 30 to its original configuration. The central tension member 35 and coil 36 components can be composed of any suitable plastic or metallic material which are typically used for steerable guidewires. The material used can also have radioopaque properties to enable remote viewing by magnetic resonance image or X-ray equipment. The steerable guidewire structure can also be composed of materials that enhance the viewing of the device using ultrasonic techniques.

Figure 9:
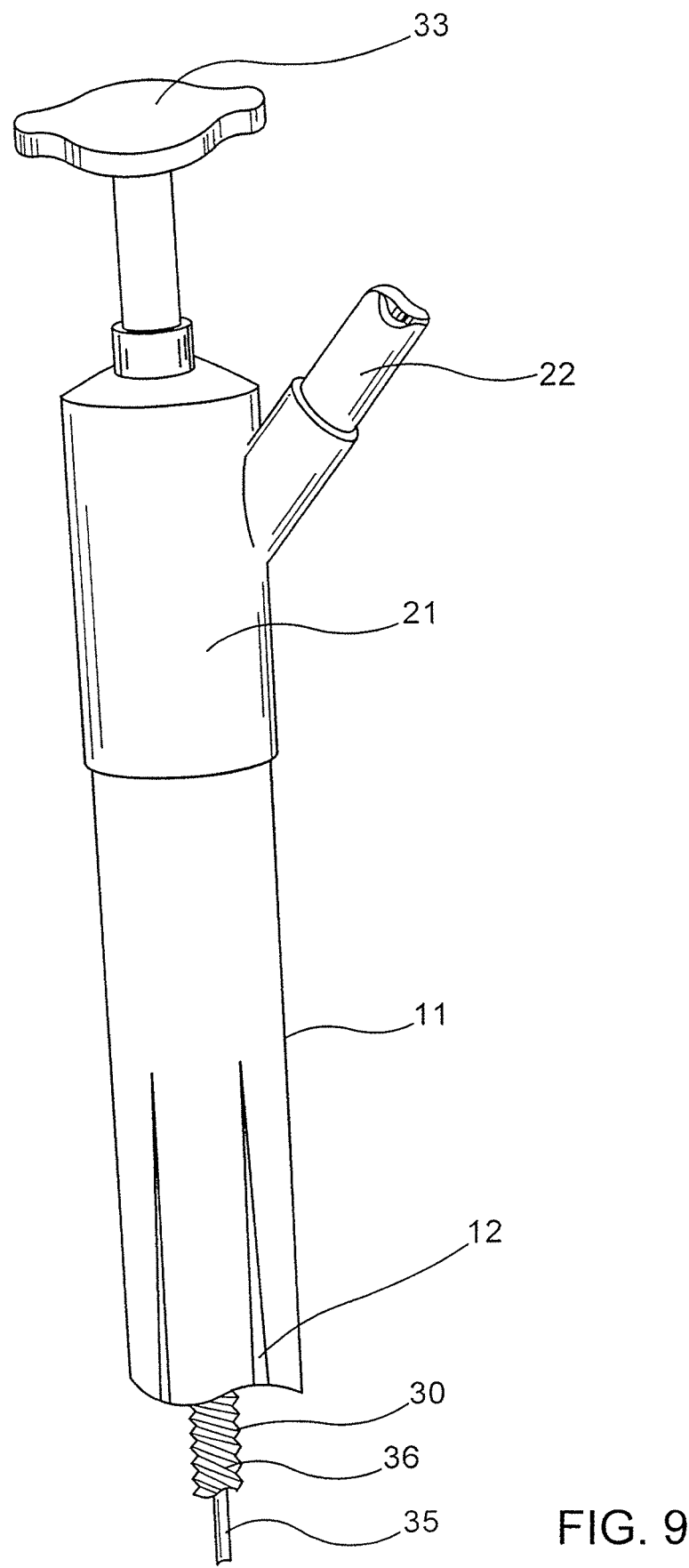
FIG. 9 is a side view of the proximal portion of the steerable wound drainage device having the external control element and exposing internal steering apparatus in accordance with one embodiment of the invention.

The external control element 33 that is mechanically coupled to the steerable guidewire structure 30 and is adapted to manipulate the configuration of the guidewire by manual operation while the distal portion of the guidewire structure resides internally within the catheter 11. In a guidewire structure containing a central tension member, the longitudinal movement of the central tension member controls the bending or flexing of the guidewire structure, and thereby controls the bending or flexing of the catheter portion from within. With respect to guidewire structures, the external control element 33 can be any conventional manually operable mechanism which controls the configuration of the guidewire. Typical external control elements which can be used in conjunction with the invention include, but are not limited to, those which are in the form of a handle, a plunger or syringe-like assembly (as shown in FIG. 9), a slidable control assembly such as that described in Falwell et al., U.S. Pat. No. 5,944,690, a pull-cable assembly such as that disclosed in Accisano, III, U.S. Pat. No. 5,571,085, the entire texts of which are incorporated herein by reference.

In one embodiment of the invention, the external control element further includes a mechanical lock which can retain or fix the desired position and configuration of the catheter for extended periods of time. In the case of a steerable guidewire structure, the mechanical lock can prevent longitudinal movement of the central tension member.

Examples of suitable internal steering apparatuses which can be used with catheters include, but are not limited to, apparatuses similar to those described in Leoni, U.S. Pat. No. 4,867,173; Fleischhacker, Jr., U.S. Pat. No. 5,069,217; Falwell et al., U.S. Pat. No. 5,944,690; and Accisano, III, U.S. Pat. No. 5,571,085, the entire disclosures of which are incorporated herein by reference.

In a preferred embodiment, the movement capabilities of the catheter portion of the wound drainage device include both transverse and rotational motion of the catheter portion, thereby enhancing the maneuvering capability of the device by the practitioner. In an even more preferred embodiment, the internal steering apparatus can be used to make the catheter portion reversibly rigid and is adapted to control the overall flexibility of the catheter portion. In other words, the internal steering apparatus has the ability to freely alternate between the rigid, semi-rigid and flexible states.

In an alternative embodiment, the internal steering means is removable and reinsertable into the catheter portion by sliding the steering means in a longitudinal direction within a steering conduit adapted to accommodate the internal steering apparatus. Accordingly, in situations where the wound drainage device is inserted into the site and the surrounding anatomy can retain its desired position, the internal steering apparatus can be removed from the device to permit the portion of the device within the body to naturally comply with the surrounding tissue. This is preferred when the wound drainage device is to be placed within the patient's body for extended periods of time, as it increases patient comfort and reduces trauma to the surround tissues.

The steering conduit 31 and internal steering apparatus can be in a variety of locations within the catheter portion of the device according to the overall design of the device. For example, the steering conduit 31 and internal steering apparatus can be located at the central longitudinal axis of the drainage catheter as shown ion FIGS. 1 through 8, or alternatively, the steering conduit 31 can be positioned between the central axis and the outer surface of the catheter body as depicted in FIG. 10, for example.

In a further embodiment, the steering conduit 31 can have a dual function as an additional fluid conduit upon removal of the internal steering apparatus. Accordingly, at least one lateral opening(s) can extend directly from the duct or exterior surface into the conduit, or intralumen opening(s) can permit communication between the internal lumen(s) and the conduit in addition to the opening(s) between the duct and internal lumen(s). Additional opening(s) directly into the conduit can serve as an alternative fluid ingress in the event the other lateral opening(s) become clogged during use.

Figure 6:
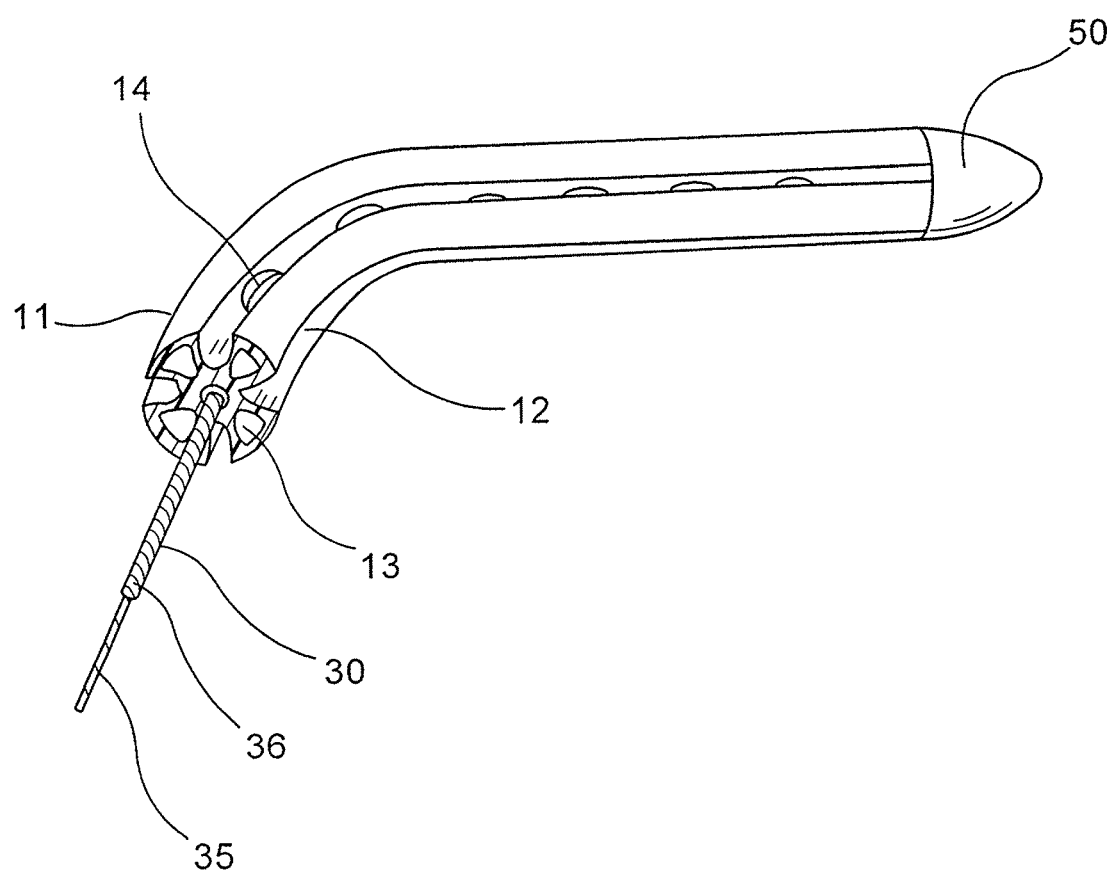
FIG. 6 is the distal portion of the device in cross-sectional view of the interior assembly having multiple ducts and lumens; and a penetration-resistant element according to one embodiment of the invention.

The distal tip of the catheter portion preferably contains a puncture-resistant element 50 which prevents the distal tip of the internal steering apparatus, such as a steerable guidewire structure 30, from perforating the end of the catheter. Such perforation is often referred to as "peeling back," and causes undesirable damage to tissues during its use. Puncture-resistant elements 50 which can be used include, but are not limited to, end caps, plug, or integrated molding of a semi-rigid material into the distal end of the catheter. Preferably, the puncture-resistant element 50 is composed of a material which is semi-rigid to afford some pliability to the catheter tip and reduce the likelihood of damage to tissue. In the case of an end-cap or plug as shown in FIGS. 6, 7 and 8, the puncture-resistant element 50 can be formed by attachment to the distal end of the catheter by adhesives, temperature welding or radiofrequency (RF) welding techniques known in the art.

To further prevent "peel back," there can be a distance between the distal end of the internal steering apparatus and the distal tip of the catheter sufficient to permit anticipated longitudinal movement of the internal steering apparatus within the steering conduit 31 during manipulation of the device. Accordingly, the wound drainage device of the invention can contain the puncture-resistant element, steering means and catheter tip distance, or a combination of both.

The overall configuration of the catheter portion of the wound drainage device can vary as well, and can be selected according to the desired characteristics of the wound drainage device as determined in light of the intended surgical site or nature of body fluid to be removed, or according to the patient's other particular needs. For example, the distal catheter portion can have an overall tubular (or cylindrical) configuration as shown in FIG. 1, or alternatively, a flattened ovular or rectangular cross-sectional configuration, or square cross-sectional configuration, for example. An ovoid configuration is depicted in FIG. 10.

The wound drainage device of the invention by way of the duct, lumen and opening features facilitates the removal of fluid from the wound site. The internal steering means permits the controlled positioning of the wound drainage device both during its initial insertion and during subsequent repositioning if needed. Accordingly, the insertion and positioning of the device of the invention can be accomplished in a manner which significantly reduces the amount of trauma to surrounding tissues and organs by enabling the practitioner to avoid unintentional damage. The ability of the wound drainage device to become rigid or semi-rigid permits insertion into the body in a forward direction by a proximally or rearwardly applied force and does not require the use of secondary guiding instruments "pull" the wound drain through the area to be drained. As a result, significantly more positioning options are available for the device of the invention.

The invention includes a kit comprising the wound drainage device of the invention together with additional surgical instruments or devices. Such instruments and devices include, but are not limited to, trocars, introducers (such as the T-Peel™ OTN Peelable Introducer available from TFX Medical, Jaffrey, N.H.), access cannulas or portals, suturing equipment, gauzes or bandages, scalpels, catheters and tubing, fluid reservoirs and collection devices, suction devices, and the like. Fluid reservoirs and collection devices which can be used in conjunction with the device of the invention include those similar to that of the Seroma-Cath® wound drainage system (available from Greer Medical, Santa Barbara, Calif.) and described in U.S. Pat. No. 4,341,212. Suction devices which can be used include conventional vacuum apparatuses and suction bulbs.

Furthermore, the wound drainage device of the invention can be used in conjunction with minimally invasive surgical procedures by virtue of its controllable features. The device can be positioned to selectively drain fluids without unnecessary damage. One example of a surgical procedure which benefits from the device of the invention is laparoscopic surgical procedures wherein careful and controlled manipulation within the abdominal cavity is needed to avoid unwanted damage to organs and connective tissues.

Another surgical procedure which can benefit from the device of the invention is ultrasound-assisted liposuction, which involves a two-stage procedure which first liquifies fat cells using an ultrasonic probe thereby leaving connective tissue, nerves and blood vessels intact. The second stage involves the use of a suction catheter to remove the liquified cells from the site. In contrast to conventional liposuction probes which involve traumatic movement within the site and indiscriminately aspirate all materials that contact the intake holes, the wound drainage device of the invention permits both controlled movement and selective material removal within a broad area. The device of the invention is structured to allow liquified fat cells to transverse the duct and permits steering (positioning and repositioning) of the device within a broad range without the need for the forcing or "ramming" motion associated with the conventional suction catheters. The full benefits of ultrasound assisted liposuction, therefore, can be realized throughout the entire procedure when using the device of the invention because the device significantly reduces the extent of damage to the vessels, nerves and connective tissues that the procedure seeks to avoid.

Another advantage of the wound drainage device of the invention is that it permits intraoperative use or use during a surgical procedure. Conventional wound drainage devices are flaccid and cannot be manipulated within the body easily. The wound drainage device of the invention is flexible enough to permit long term use, while at the same time rigid enough and controllable to permit repositioning to avoid interference with surgical instruments during surgical procedures.

INDUSTRIAL APPLICABILITY

The wound drainage device of the invention allows medical practitioners to exercise significantly greater control over the placement of the device in the patient. The inventive device also provides improved drainage catheter features. Accordingly, unnecessary trauma to surrounding tissues and organs can be avoided thereby increasing patient comfort and expediting healing and recovery.

The complete disclosures of all patents, patent applications, and publications are incorporated herein by reference as if each were individually incorporate by reference. The invention has been described with reference to various specific and preferred embodiments and techniques. However, it should be understood that many variations and modifications can be made while remaining within the spirit and scope of the invention.

What is claimed is:

1. A wound drainage device comprising:
    a flexible catheter having a body and a plurality of drainage ducts defined therein;
    a steering conduit, wherein the body of the catheter encloses the steering conduit, wherein the plurality of drainage ducts are arranged around the steering conduit and extend circumferentially relative to the steering conduit, and wherein only the body of the catheter is located directly between an outer circumference of the steering conduit and the plurality of drainage ducts;
    an internal steering apparatus at least partially disposed within the steering conduit and structured to controllably position the catheter within a body by causing deviation of the catheter into a plurality of configurations and directions relative to a longitudinal axis of the catheter; and
    at least one lateral opening is defined in a bottom surface of a corresponding longitudinal duct of the plurality of longitudinal ducts;
    wherein the internal steering apparatus is configured to selectively alter an effective rigidity of the catheter while the internal steering apparatus is disposed within the steering conduit.

2. The wound drainage device of claim 1, wherein the at least one lateral opening defines an area that is smaller than an area defined by the bottom surface of the corresponding longitudinal duct.

3. The wound drainage device of claim 1, wherein the at least one lateral opening extends circumferentially relative to the steering conduit.

4. The wound drainage device of claim 1, wherein the plurality of drainage ducts comprises a plurality of internal lumens defined in the catheter.

5. The wound drainage device of claim 1, wherein the catheter further comprises:
    a first proximal opening fluidly connected to the steering conduit;
    wherein upon final assembly, a first portion of the internal steering apparatus is disposed within the steering conduit and a second portion of the internal steering apparatus extends externally from a second proximal opening; and
    wherein the first proximal opening is distal the second proximal opening.

6. The wound drainage device of claim 1, wherein:
    the internal steering apparatus comprises a steerable guidewire structure; and
    the steerable guidewire is slidably disposed within the steering conduit.

7. The wound drainage device of claim 6, wherein the steerable guidewire terminates at a distal tip sized to be freely movable through the steering conduit, such that the steerable guidewire is fully removable from the catheter.

8. The wound drainage device of claim 4, wherein the catheter further comprises:
    a first proximal opening fluidly connected to the plurality of internal lumens; and
    a second proximal opening fluidly connected to the steering conduit;
    wherein, upon final assembly, a first portion of the internal steering apparatus is disposed within the steering conduit and a second portion of the internal steering apparatus extends externally from the second proximal opening.

9. The wound drainage device of claim 8 wherein the second proximal opening is distal the first proximal opening.

10. The wound drainage device of claim 9, wherein the second proximal opening comprises a radial passage through a side wall of the catheter.

11. The wound drainage device of claim 8, wherein the first proximal opening is distal the second proximal opening.

12. The wound drainage device of claim 8, wherein the steering conduit has a cross-sectional area that is less than a cross-sectional area of each internal lumen.

13. The wound drainage device of claim 6, wherein the steerable guidewire terminates at a distal tip sized to be freely movable through the steering conduit, such that the steerable guidewire is fully removable from the catheter.

14. The wound drainage device of claim 1, wherein the internal steering apparatus includes:
    a central tension member;
    a coil surrounding the tension member; and
    a handle connected to the tension member and the coil;
    wherein, upon final assembly of the device, the tension member and the coil are at least partially disposed within the catheter, and the handle is external the catheter.

15. The wound drainage device of claim 14, wherein the internal steering apparatus is configured such that movement of the handle effectuates transverse movement, rotational movement, and flexibility state change of the catheter.

16. The wound drainage device of claim 14, wherein the internal steering apparatus is configured to be freely operable among rigid, semi-rigid, and flexible states.

* * * * *